United States Patent
McClure

(10) Patent No.: US 6,659,968 B1
(45) Date of Patent: Dec. 9, 2003

(54) ACTIVITY MONITOR FOR PAIN MANAGEMENT EFFICACY MEASUREMENT

(75) Inventor: Kelly H. McClure, Simi Valley, CA (US)

(73) Assignee: Advanced Bionics Corporation, Sylmar, CA (US)

(*) Notice: Subject to any disclaimer, the term of this patent is extended or adjusted under 35 U.S.C. 154(b) by 317 days.

(21) Appl. No.: 09/862,242

(22) Filed: May 22, 2001

Related U.S. Application Data

(60) Provisional application No. 60/208,715, filed on Jun. 1, 2000.

(51) Int. Cl.[7] ................................................ A61B 5/11
(52) U.S. Cl. .............................. 600/595; 705/3; 607/46; 607/116
(58) Field of Search ................................. 600/300, 301, 600/594, 595; 607/43, 46, 19, 30, 32, 60, 62, 116, 117; 435/18, 19, 20; 705/2, 3; 702/19, 130, 141, 190, 191

(56) References Cited

U.S. PATENT DOCUMENTS

| | | | | |
|---|---|---|---|---|
| 3,646,940 A | | 3/1972 | Timm et al. ................. 128/421 |
| 3,724,467 A | | 4/1973 | Avery et al. ................. 128/418 |
| 3,822,708 A | | 7/1974 | Zilber ......................... 128/419 |
| 4,505,275 A | | 3/1985 | Chen .......................... 128/421 |
| 5,370,672 A | | 12/1994 | Fowler et al. ................ 607/58 |
| 5,375,610 A | * | 12/1994 | LaCourse et al. ........... 600/595 |
| 5,573,013 A | * | 11/1996 | Conlan ........................ 600/595 |
| 5,653,739 A | | 8/1997 | Maurer et al. ................ 607/46 |
| 5,893,883 A | | 4/1999 | Torgerson et al. ............ 607/59 |
| 5,938,690 A | | 8/1999 | Law et al. .................... 607/46 |
| 6,102,874 A | * | 8/2000 | Stone et al. ................. 600/595 |
| 6,120,467 A | | 9/2000 | Schallhorn .................. 600/595 |
| 6,440,090 B1 | * | 8/2002 | Schallhorn .................. 600/595 |
| 2001/0037222 A1 | * | 11/2001 | Platt et al. ..................... 705/3 |
| 2002/0052562 A1 | * | 5/2002 | Lipman ....................... 600/300 |
| 2002/0068960 A1 | * | 6/2002 | Saberski et al. .............. 607/46 |
| 2002/0086343 A1 | * | 7/2002 | Cameron et al. ............. 435/20 |

* cited by examiner

*Primary Examiner*—Willis R. Wolfe
(74) *Attorney, Agent, or Firm*—Kenneth L. Green; Philip H. Lee; Bryant R. Gold

(57) ABSTRACT

An activity monitoring system measures the effectiveness of pain management using using data from motion or activity sensors attached to the patient's body to compute measures of exertion level of a patient. Increased levels of exertion are an indication of successful pain management. The patient's walking gait smoothness and walking gait stability are also graded as indicators of pain management effectiveness. The motion or activity sensors may be part of a temporary stimulation system used during percutaneous trials, part of a permanent implanted system, or an independent sensor package carried on the patient's body. The particular location and axes of the motion or activity sensors may be chosen based on the location of the pain being treated. The effectiveness of a particular pain management stimulation parameter set is based on the statistics accumulated over a period of time, for example one hour.

14 Claims, 5 Drawing Sheets

ACTIVITY MONITOR FOR PAIN MANAGEMENT EFFICACY MEASUREMENT

The present application claims the benefit of U.S. Provisional Application Serial No. 60/208,715, filed Jun. 1, 2000, which application is incorporated herein by reference.

BACKGROUND OF THE INVENTION

The present invention relates to Spinal Cord Stimulation (SCS) systems and more particularly to a system and method for measuring the effectiveness of SCS system stimulation parameter sets (also known as protocols). An SCS system treats chronic pain by providing electrical stimulation pulses, through the electrodes of an electrode array, which electrode array is placed epidurally near a patient's spine. The stimulation parameter set determines what stimulation pulses are used with the electrode array. The optimal stimulation parameter set for a specific patient may only be determined from empirical evidence of the stimulation parameter set's success. Therefore, an effective method of measuring the efficacy of candidate stimulation parameter sets is an important tool in tuning the SCS system to achieve effective pain reduction.

Spinal cord stimulation is a well accepted clinical method for reducing pain in certain populations of patients. SCS systems typically include an Implantable Pulse Generator (IPG), electrodes, and electrode lead extensions connecting the IPG to the electrodes. The IPG generates electrical pulses that are delivered, through the electrodes, to the dorsal column fibers within the spinal cord. The electrodes are implanted along the dura of the spinal cord. Individual electrode contacts (the "electrodes") are arranged in a desired pattern and spacing in order to create an electrode array. Individual wires, or electrode leads, connect with each electrode in the array. The electrode leads exit the spinal column and attach to one or more electrode lead extensions. The electrode lead extensions, in turn, are typically tunneled around the torso of the patient to a subcutaneous pocket where the IPG is implanted.

Spinal cord stimulators and other stimulation systems are known in the art. For example, an implantable electronic stimulator is disclosed in U.S. Pat. No. 3,646,940 that provides timed sequenced electrical impulses to a plurality of electrodes. As another example, U.S. Pat. No. 3,724,467 issued Apr. 3, 1973 for "Electrode Implant For The Neuro-Stimulation of The Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes which are positioned longitudinally on the spinal cord. Electrical pulses applied to the electrodes block perceived intractable pain, while allowing passage of other sensations. A patient operated switch allows the patient Most of the electrode arrays used with known SCS systems employ between 4 and 16 electrodes. Electrodes are selectively programmed to act as anodes and cathodes, creating a stimulating group. The number of stimulation groups available, combined with the ability of integrated circuits to generate a variety of complex stimulation pulses, presents a multiplicity of stimulation parameter sets to the clinician. A known method of evaluating the efficacy of competing stimulation parameter sets is the walking test, wherein the clinician observes the patient walk before and after the therapy is applied. The effectiveness of the therapy is judged based on the clinician's subjective observations of the patent's gait, etc. This method clearly has the disadvantages of lacking an objective measure, and failing to provide an ongoing analysis of the efficacy of the stimulation parameter set once the patient leaves the clinician's office.

A system and method for monitoring patient activity and adjusting stimulation parameters is described in U.S. Pat. No. 6,120,467. The system described in the '467 patent computes both long term and short term averages of the filtered output of a sensor carried on a patient, which sensor is preferably an accelerometer. The filter filters out noise in the sensor output. The short term average is divided by the long term average to compute a normalized average. Thresholds are preset for rest, moderate activity, and vigorous activity levels. The normalized average is compared to the thresholds, and the amount of time that the normalized average fits each category of activity is stored. Any adjustments made by the patient to the therapy are also recorded and time tagged to allow time alignment with the activity recording. The stored values are later provided to a physician to provide an objective measure of stimulation effectiveness to compare with subjective evaluation provided directly by the patient. The physician may then objectively interpret the subjective patient information.

While the system and method taught by the '467 patent may provide some advantages over a purely subjective approach, there are several disadvantages to the approach of the '467 patent. The sensor data is filtered to remove noise, not to specifically pass data corresponding to selected activities. The normalizer may ignore long periods of activity, such as long walks, if the long term average is not substantially longer than the period of activity. Further, a period of very light activity, surrounded by periods of no activity, may be falsely normalized to a high activity value, Finally, the method of the '467 patent relies on the assumption that a higher activity level is always an indication of improved stimulation. However, in many cases a patient may fidget due to discomfort, and thus the increased activity may be an indication of failure, not success.

What is therefore needed is a method of evaluating the effectiveness of candidate SCS stimulation parameter sets, wherein the evaluation method is objective in nature, is not subject to normalizer induced errors, targets specific physical activities, and continues to monitor the patient's activity in the absence of visits to the clinician's office.

SUMMARY OF THE INVENTION

The present invention addresses the above and other needs by providing an activity monitor for measuring the effectiveness of a Spinal Cord Stimulation (SCS) system. The activity monitor includes at least one motion or activity sensor which may be incorporated into a temporary stimulator, integrated into an implanted stimulator, or worn as a separate external stand-alone device. The output of the sensor is filtered to pass data associated with defined activities, and processed to measure the level of activity of a patient. Increased levels of targeted activities are an indication of successful pain management. Additionally, a walking gait monitor is used to evaluate the stability and smoothness of the patient's walk as a further indication of successful pain management. In a preferred embodiment, the activity monitor provides feedback to an update stimulation parameters function to enable long term tuning of stimulation parameters.

In accordance with one aspect of the invention, there is provided an activity monitor which can be used with a temporary SCS system during the percutaneous trial. Such a temporary activity monitor allows the clinician to objectively evaluate both the applicability of SCS to a particular patient, and to compare the effectiveness of alternative electrode positions and stimulation waveforms.

It is a feature of the invention that the activity monitor used with the system may be integrated into an implantable SCS system to monitor pain management effectiveness over a long time period. Various stimulation parameter sets are available for execution once a permanent implantable stimulator is in place. Such stimulation parameter sets define various waveforms and combinations of electrodes. The ability to evaluate the effectiveness of a multiplicity of stimulation parameter sets, over a long period of time, permits a clinician to determine the best overall stimulation parameter set for a patient. And, as physiological changes take place over time, the system may continue to monitor the effectiveness of the pain management and provide the results to a clinician.

It is an additional feature of the invention to provide a temporary external device that may be strapped or otherwise carried on the body of a patient. Such a temporary device includes a motion sensor attached securely to the body of the patient to measure motion, a signal processor, and a recording device. The temporary device provides a capability to periodically reevaluate the effectiveness of an SCS system, which SCS system does not include an integrated monitoring system.

It is a feature of each of the above described embodiments of the present invention to filter sensor data to pass signals associated with activities of interest. The filtered sensor data is used to compute the variance of the output of a motion sensor as an estimate of the exertion level of a patient. Such a measure of exertion is an indication of the effectiveness of pain management because the presence of pain has the effect of causing a patient to minimize movement.

It is a further feature of the invention to analyze the motion sensor output to measure the stability and smoothness of a walking gait, or other identified activity, of a patient. Some types of pain are triggered by the act of walking, and a patient alters their walking gait to avoid such pain. The analysis of the walking gait provides a capability to detect such pain avoiding behavior.

It is another feature of the invention to identify the present activity of a patient, thereby allowing the system to limit data collection to defined activities, such as walking.

It is additionally a feature of the invention to provide a feedback mechanism for SCS systems to allow the systems to search for the most effective SCS stimulation parameter set for a patient. The SCS system measures the effectiveness of various SCS stimulation parameter sets over a period of time. The stimulation parameter set that provides the most effective overall pain management is selected for use. Later, as physiological conditions change in a patient, the SCS system can re-adapt to the developing environment and continue to offer effective pain management.

It is another feature of the invention to provide a patient override control. Such an override control provides the patient a means to immediately cancel the selection of a new stimulation parameter set, which stimulation parameter set may have resulted in unpleasant sensations or an increase in perceived pain.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
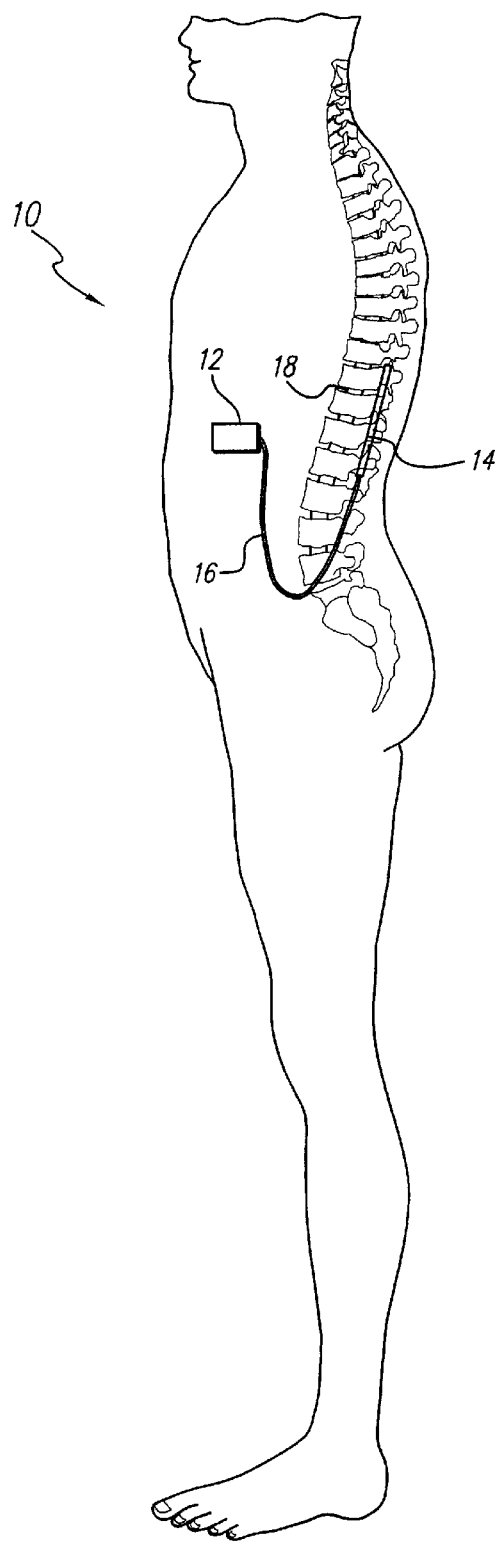
FIG. 1 depicts a typical embodiment of a Spinal Cord Stimulation (SCS) system implanted in a patient.

Many patients who suffer from chronic pain are helped through the application of pain management systems in the form of chemical or electrical implants. An example of an electrical implant is a Spinal Cord Stimulation (SCS) system used to treat chronic pain, as shown in FIG. 1. The SCS system is implanted in a patient 10. The SCS system includes an Implantable Pulse Generator (IPG) 12 that generates the electrical signal used for stimulation. An electrode array 14 is connected to the IPG 12 by a lead extension 16. The stimulation is delivered by the electrode array 14 to the spinal cord 18. Such stimulation, when properly performed, has the effect of blocking sensed pain while not Interfering with other nerve functions.

However, each patient is unique and the pain management system must be fitted to each individual patient to achieve the best performance. Fitting the system to a patient involves adjusting the placement of the electrode array 14 and the stimulation signal generated by the IPG 12. A set of parameters defining the electrode locations, and the stimulation signal, shall hereafter be referred to as a stimulation parameter set. The process of fitting an SCS system to a patient comprises comparing the reduction of pain achieved by one stimulation parameter set to that achieved by another stimulation parameter set. The reduction in pain generally results in a greater activity level (hereafter referred to as exertion) by a patient, and by a more natural movement (for example, walking gait). As previously described, existing methods use a "walking test" in which a clinician observes the patient walk and subjectively assesses the effectiveness of pain management. The present invention replaces the subjective walking test by providing a monitoring system, which monitoring system measures the motion of one or more points on the body of the patient. The measurements are processed to determine the exertion level of the patient, and the stability and smoothness of the walking gait. Additionally, the measurements are processed to identify the activity type (e.g., walking) during the data collection period. The exertion level, and gait stability and smoothness, are then tagged with the activity type and a description of the stimulation parameter set is use while the data is generated, and stored for later analysis.

The monitoring system of the present invention may be exercised during the fitting process to evaluate the effectiveness of SCS to a patient and to select a stimulation parameter set. During the fitting process, the monitoring systems provide a measure of the effectiveness of various electrode positions in addition to the effectiveness of various stimulation parameter sets. The monitoring system may also be used on a long term basis to track the effectiveness of the selected stimulation parameters and to detect physiological changes in a patient that affect the effectiveness of the pain management system.

Figure 2:
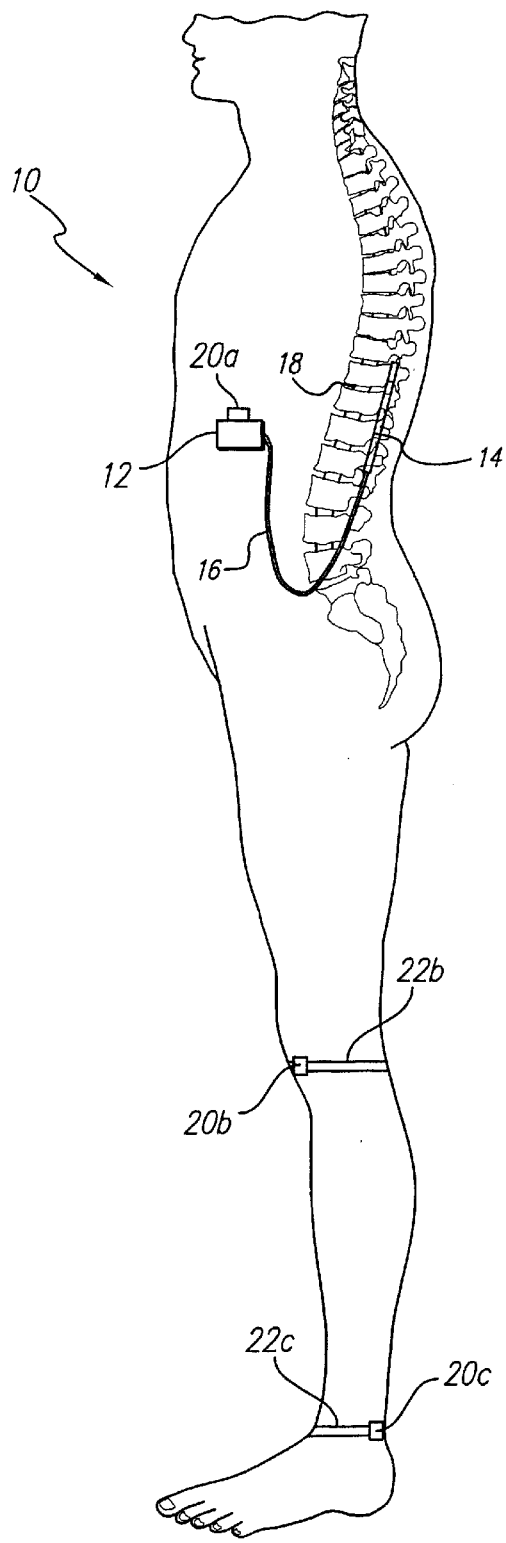
FIG. 2 depicts motion sensors of the present invention implanted in a patient or carried on a patient.

Motion of a patient may be measured by sensor apparatus 20a–20c shown in FIG. 2. The required number and location of the sensor apparatus 20a–20c varies based on the characteristics of the pain the patient is experiencing, and is determined by a clinician. Placing the sensor apparatus 20b, 20c on points where motion is greatest results in the clearest signal but may require either additional sensors and wiring, or that the sensor apparatus 20b, 20c include stand-alone signal processing and memory capability. The sensor apparatus 20b, 20c are most appropriate for temporary use as in percutaneous trials where the sensor apparatus 20b, 20c may be temporarily connected by wires to a temporary stimulator. The sensor apparatus 20b, 20c may be held in place by sensor straps 22b, 22c.

Alternatively, a sensor apparatus 20a located near the waist of the patient may provide adequate measurements and avoid the cost and complexity resulting from other sensor apparatus 20b, 20c. The adequacy of a single sensor apparatus 20a ultimately depends on the nature of the pain being treated. The sensor apparatus 20a may be carried as a separate device, or integrated into either a permanent or temporary stimulator.

In practice, the locations of sensor apparatus 20a–20c may vary widely, as may the means of retaining the sensor apparatus. Upon observing a patient, a clinician (e.g., a physician or any health care professional providing these services) ascertains the effects of pain on the movement of the patient, and determines where to place the sensor apparatus to best monitor the effects. Those skilled in the art will recognize various locations and retaining devices for the sensor apparatus, and it is intended that these variations fall within the scope of the present invention.

Figure 3:
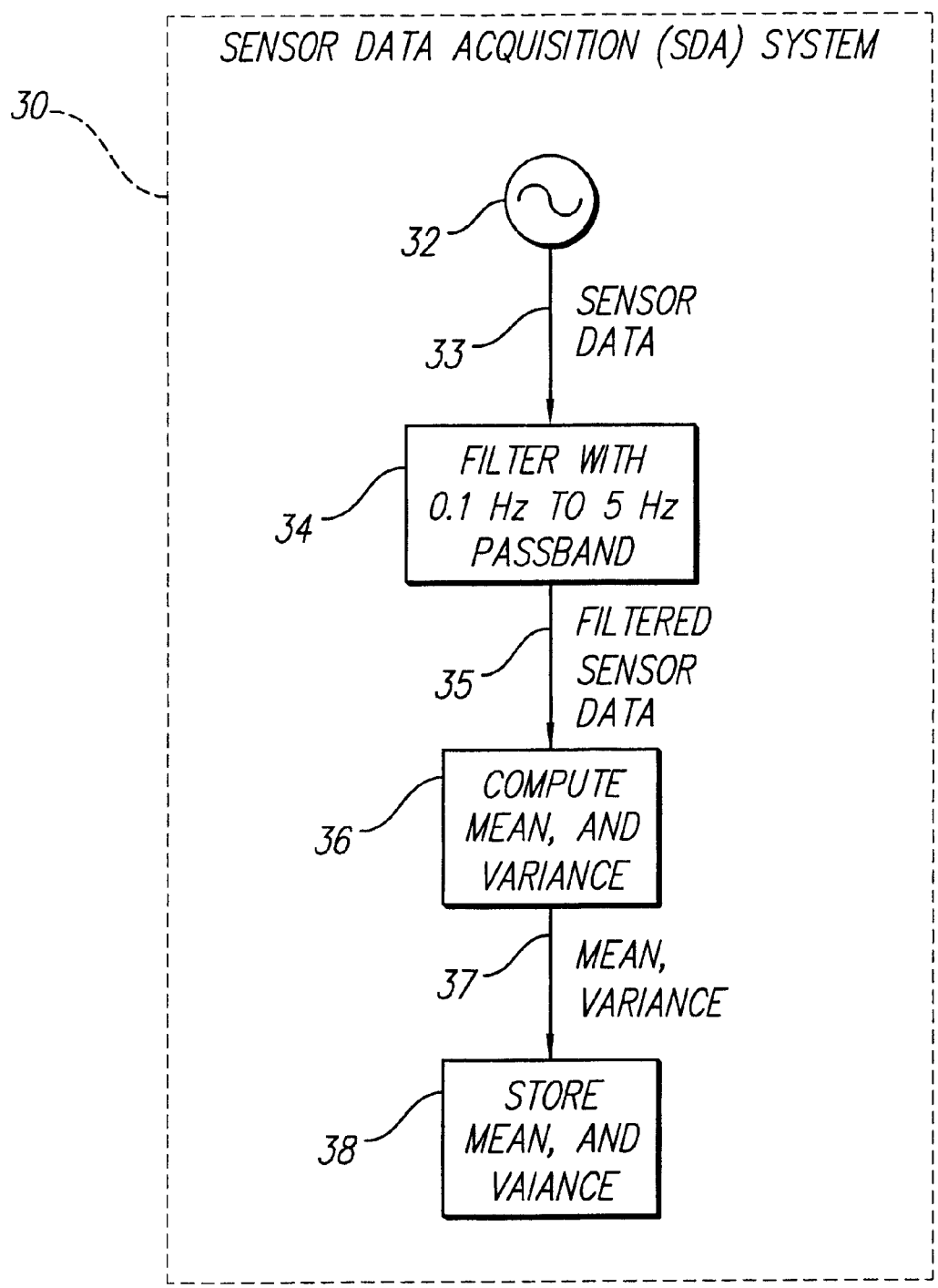
FIG. 3 shows a functional flow of a Sensor Data Acquisition (ADA) system for an activity monitoring system.

A functional flow diagram for a monitor comprising a Sensor Data Acquisition (SDA) system 30 is shown in FIG. 3. A sensor 32, preferably one or more accelerometers, senses the motion of a point on the body of the patient 10. The resulting sensor data 33 is first processed by a bandpass filter 34 to generate filtered sensor data 35. The motion of interest is generally in the 2 Hz to 3 Hz frequency range, and the pass band of the bandpass filter 34 is preferably 0.1 Hz to 5 Hz. The sample rate is preferably 10 Hz to satisfy the Nyquist criteria. Next, a processor 36 preferably computes a mean and variance 37 of the filtered sensor data 35 from a data sequence sufficiently long to compute meaningful statistics, e.g., a sequence that is two seconds long. Lastly, the mean and variance 37 are stored in memory 38 for subsequent analysis. Those skilled in the art will recognize that other statistical measures may be substituted for the mean and variance, and the other measures are intended to come within the scope of the present invention.

The SDA system 30 described in FIG. 3 may ideally be used to accumulate data during percutaneous trials where a clinician observes the patient during data collection, and the clinician is aware of the activity of the patient during data collection. Following the test, the clinician retrieves the stored data, which data may then be analyzed for comparison with other data collected using other stimulation parameter sets, or analyzed independently to ascertain the efficacy of pain management for a specific patient.

Although an accelerometer is a preferred sensor, other sensors may be used in many applications. Angular motions of limbs may be measured by gyroscopes, and strain gauges may be employed to sense muscle use. The data collection rates and filtering band recited above are based on monitoring the effect pain has on walking. Those skilled in the art will recognize that cases arise where sensed pain affects a patient in other ways. In these other cases the present invention is equally applicable but may require changes to data rates and signal filtering.

Similarly, part or all of the on-board processing and memory may be replaced by telemetry to a separate off-board receiver, which receiver may contain a data processing and or recording function, or which receiver may be connected to a personal computer or work station. Those skilled in the art will recognize that these and other various allocations of functions fall within the scope of the present invention.

Figure 4:
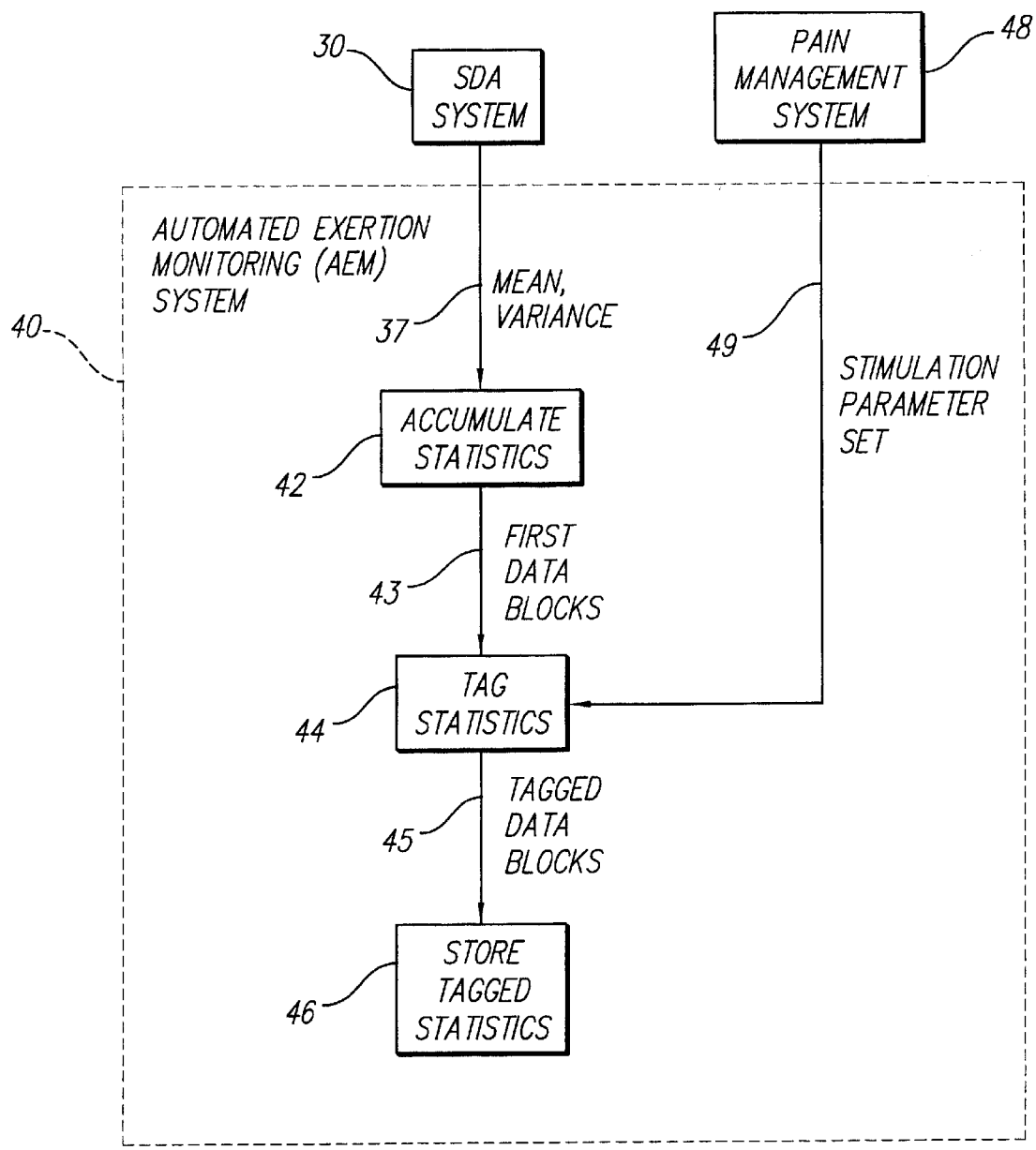
FIG. 4 shows a functional flow of an Automated Exertion Monitoring (AEM) system for collection of exertion measurements.

A functional flow diagram for a monitor comprising an Automated Exertion Monitoring (AEM) system 40 is shown in FIG. 4. The AEM system uses the mean and variance 37 as inputs computed by the SDA system 30. Additionally, a pain management system 48 provides a stimulation parameter set 49 presently being exercised. Accumulate statistics module 42 accumulates mean and variance 37 values into first data blocks 43. The number of samples in a first data block 43 is variable and is determined by the clinician based on activities that the patient 10 is expected to perform during the data collection period. When no information is available for determining the data block length, the data block length is set to a predetermined value, preferably 1 hour. Tag statistics module 44 generates tagged data blocks 45 by tagging each first data block 43, with the stimulation parameter set 49 in use when the data in the first data block 43 is collected. The tagged data blocks 45 may also contain an additional flag indicating the activity type 57. The activity type 57 is described below for FIG. 5. Store tagged statistics module 46 stores the tagged data blocks 45 for later analysis. The AEM system 40 may be integrated into the SCS system, which AEM system 40 uses miniature accelerometers. In such an integrated system, the processing described in FIG. 4 may be performed in the IPG, or in a separate processor.

As in the case of the SDA system 30, the functions performed by the AES system 40 may be allocated between on-board processors and off-board processors. In the case of the SDA system 40, the use of telemetry and off-board processors may prove less advantageous than in the case of the SDA system 30 because the AES system 40 typically monitors pain management performance over a very long period, during which period it may not be likely that a patient will remain in a fixed area. But, in some cases where telemetry to a local receiver and processor is feasible, the allocation of filtering, data processing, and data recording, to an off-board device may be advantageous due to cost savings and the greater processing power of an off-board processor.

Figure 5:
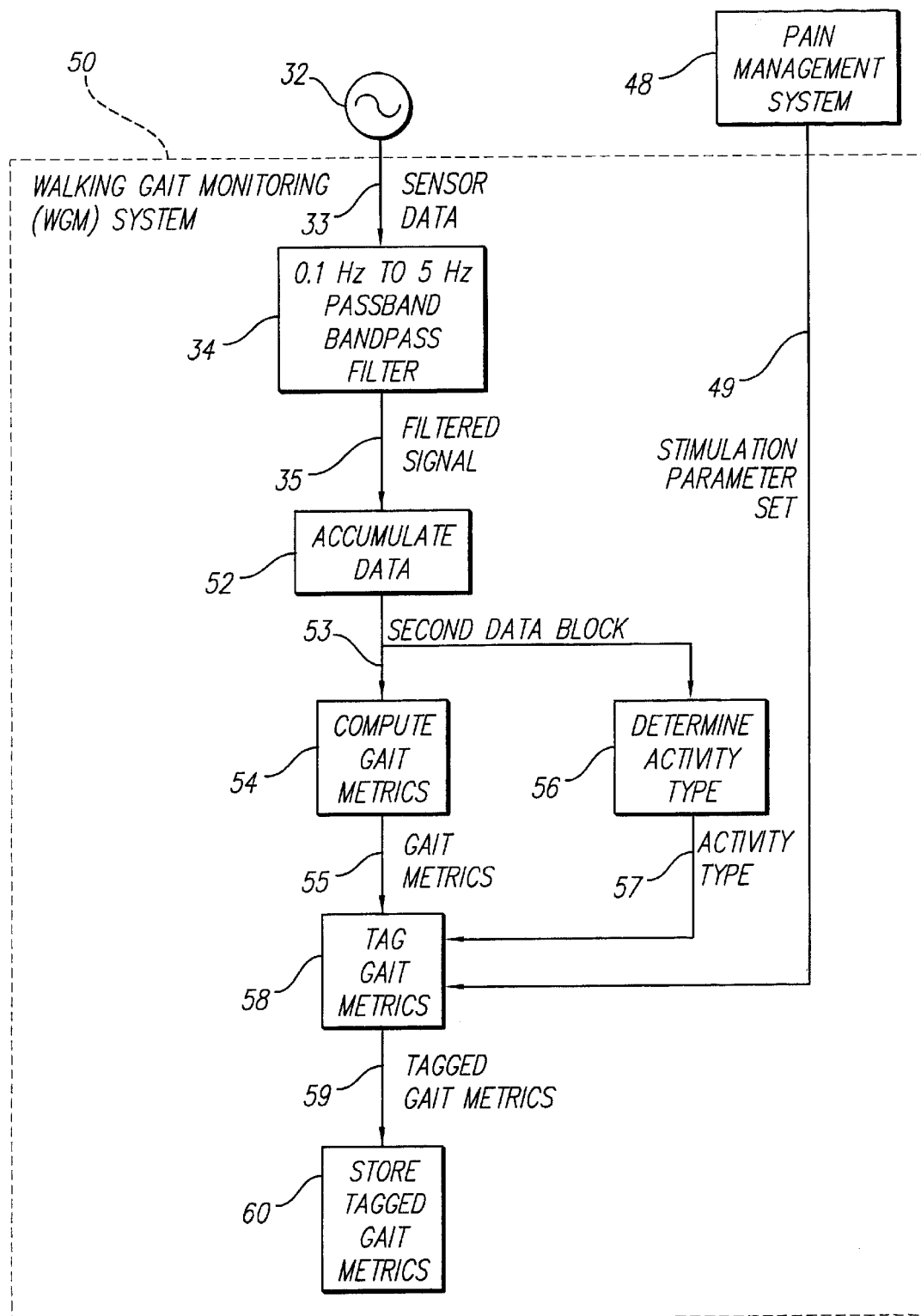
FIG. 5 shows a functional flow of a Walking Gait Monitoring (WGM) system for collection of gait measurements.

A monitor in accordance with the present invention may also utilize a measure of performance based on the stability and smoothness of a patient's walk. A functional flow diagram for such a monitoring system, a Walking Gait Monitoring (WGM) system 50, for monitoring pain management based on a walking gate stability measure and a walking gait smoothness measure, is shown in FIG. 5. The WGM 50 receives sensor data 33 from the sensor 32. The sensor data 33 is filtered by the bandpass filter 34 as described in FIG. 3 above for the SDA system 30 to generate filtered signal 35. The filtered signal 35 is processed by an accumulate data module 52 whereby second data blocks 53 are formed. The second data blocks 53 are provided to a compute gait metrics module 54 where the stability and smoothness of the gait are graded to generate gait metrics 55. Such grading is based on either a default criteria or upon criteria established by the clinician during the temporary percutaneous trials. The grading may compare cycles within the filtered signal, compare the filtered signal 35 to at least one example of a smooth stable gait, or be based on the spectral content of the filtered signal 35. The stability of the gait may be graded by comparing consecutive cycles of the walking gait and determining the variation from cycle to cycle. The walking gait smoothness may be analyzed by first warping the filtered signal 35 to overlay the example, and then measuring the deviation of individual points of the filtered signal 35 from the example. The compute gait metrics module 54 outputs the gait metrics 55. Other methods of measuring gait stability and gait smoothness may prove useful due to variations in the effect pain has on the patient, and are within the scope of the present invention.

A determine activity type module 56 operates in parallel with the compute gait metrics module 54. The determine activity type module 56 analyzes the second data blocks 53 to determine if the second data block supports the hypothesis that the patient is walking. Data will typically be collected during the temporary percutaneous trails by the clinician. The clinician will designate at least one data set that is representative of walking. This data set will be compared to subsequent data to classify the subsequent data as corresponding to walking or as not corresponding to walking. The comparison may be based on a direct time domain comparison of sensor data, or a frequency domain comparison. A third method is to use a neural network trained on the temporary percutaneous data and later used to classify second data blocks 53. A resulting activity type 57 is output.

Continuing with FIG. 5, tag gait metrics module 58 receives both the gait metrics 55 and the activity type 57 and generates tagged gait metrics 59, which tagged gait metrics 59 may also be referred to herein as "a second tagged data block", or similar language. The message containing the gait metrics 55 is tagged with the activity type 57 that was identified for the second data block 53 from which the gait metrics 55 were computed. A store tagged gait metrics module 60 receives the tagged gait metrics 59 and stores the results for subsequent evaluation.

Figure 6:
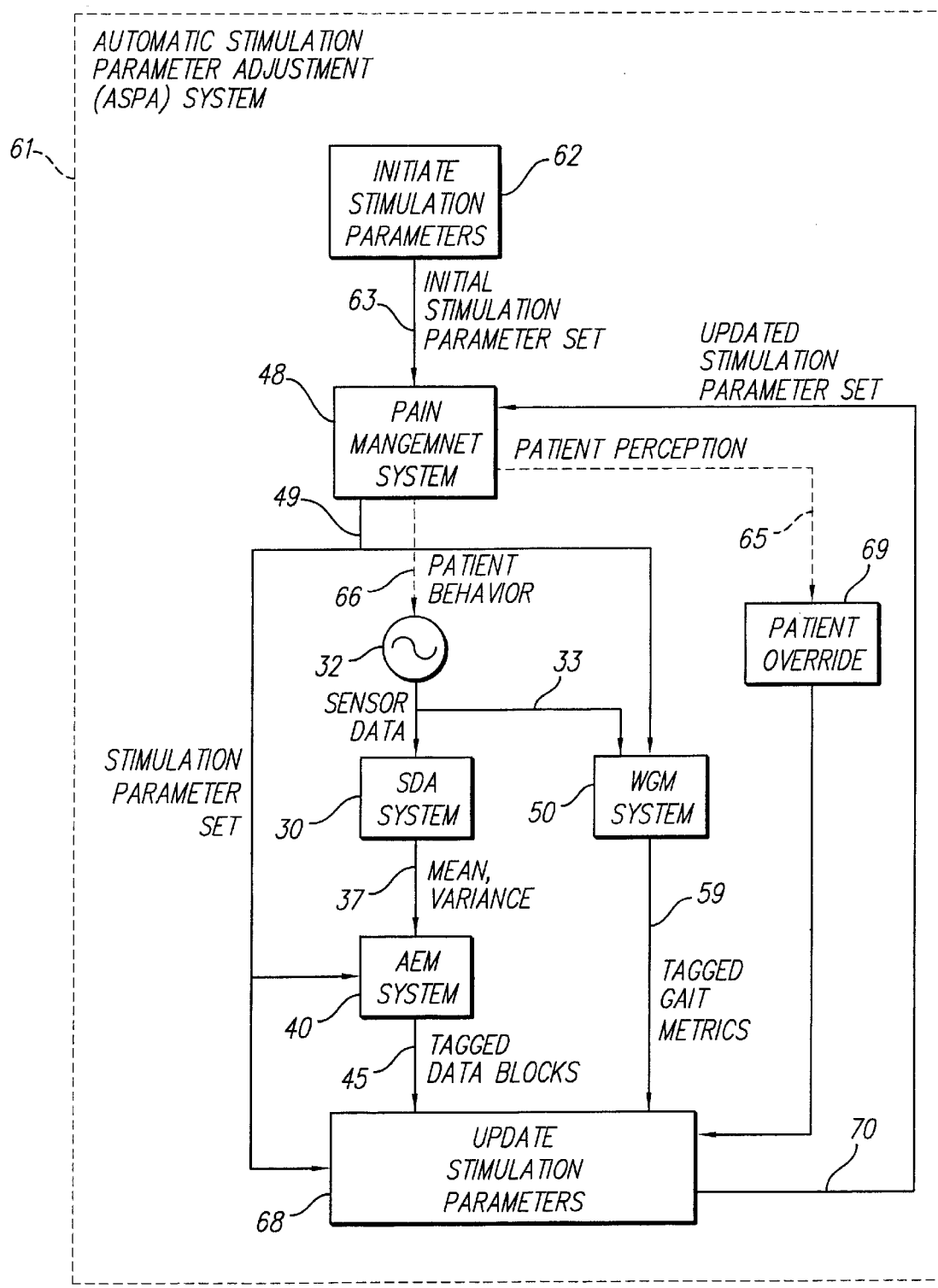
FIG. 6 shows a functional flow for an Automated Stimulation Parameter Adjustment (ASPA) system.

A functional flow diagram for an Automatic Stimulation Parameter Adjustment (ASPA) system 61 is shown in FIG. 6. The ASPA system 61 is created from a combination of a pain management system 48, the pain management monitoring systems described above in FIGS. 3, 4, and 5, and an update stimulation parameters module 68. The ASPA system 61 integrates the monitoring systems with the pain management system 48 and serves to finely tune stimulation parameters following the initial fitting of the pain management system 48, or may operate over the life of the pain management system 48 to adjust the stimulation parameters for physiological changes in the patient 10.

The ASPA system 61 includes an initial stimulation parameters module 62 which provides an initial stimulation parameter set 63 to the pain management system 48. The initial stimulation parameter set 63 is used as a starting point for the pain management system 48, and is established in an initial fitting, or re-established in a subsequent fitting by a clinician. The effects of the pain management system 48 using the initial stimulation parameter set 63 are provided to the sensor 32 through a patient behavior 66. The sensor 32 provides sensor data 33 to the SDA system 30 and the WGM system 50. The SDA system 30 calculates the mean and variance 37 of the sensor data 33 and provides the mean and variance 37 to the AEM system 40. The AEM system 40 provides tagged data blocks 45 to an update stimulation parameters module 68. Additionally, the WGM system 50 provides tagged gait metrics 59 to the update stimulation parameters module 68. The AEM system 40 is described In FIG. 4 above, and the WGM system 50 is described in FIG. 5 above.

The update stimulation parameters module 68 monitors the tagged data blocks 45 and the tagged gait metrics 59. During initial operation the stimulation parameter set 49 remains set to the initial stimulation parameter set 63. When sufficient data has been collected to characterize the effectiveness of the initial stimulation parameter set 63, the update stimulation parameters module 68 begins a process of searching for a set of updated stimulation parameters 70. The search for the updated stimulation parameters 70 may be one of several forms. To ensure patient comfort and safety, the changes are small in each case. In a first embodiment, the search is performed over sets of predefined stimulation parameter sets predetermined by a clinician. In a second embodiment, small random variations are made in stimulation parameters. In both the first and the second embodiments of the searches, the update stimulation parameters module 68 selects a candidate stimulation parameter set, and then collects data for that set. If the candidate stimulation parameter set results in better pain management effectiveness, the candidate stimulation parameter set is selected as the stimulation parameter set.

In a third embodiment of the search, a gradient method is applied. The gradient method applies very small perturbations to the stimulation parameter set 49. The perturbations define candidate stimulation parameter sets which deviate in several different directions away from the present stimulation parameter set. After all of the candidate stimulation parameter sets have been tested, the perturbation that provides the greatest improvement in pain management effectiveness is selected as the best perturbation. The update stimulation parameters module 68 then begins to step in the direction defined by the best perturbation. Consecutive steps are made, and the effectiveness of the resulting set of updated stimulation parameter set 70 is evaluated. As long as the updated stimulation parameter set 70 results in improved pain management, the direction of change is unaltered. When a reduced effectiveness of pain management is detected, the gradient search is again executed about the previous updated stimulation parameter set 70 that showed improved effectiveness, and the entire process is repeated.

Those skilled in the art will recognize that many other search methods exist and may be exercised with the present invention. The method of searching is not an essential element of the present invention, and it is intended that these other methods fall within the scope of the present invention.

In all cases, the update stimulation parameters module 68 closely monitors the performance of the pain management 64 in the period immediately following a change in stimulation parameters. If any clear indication of increased pain is present, the stimulation parameters are reset to the previous values. Such indications include any immediate and unusual sensor measurements. Additionally, a patient override feature 69 is provided to allow the patient to reset the pain management 64 to the prior stimulation parameter set should the patient perception 65 indicate discomfort. In a preferred embodiment, the patient override feature 69 includes a radio frequency remote control.

While the invention herein disclosed has been described by means of specific embodiments and applications thereof, numerous modifications and variations could be made thereto by those skilled in the art without departing from the scope of the invention set forth in the claims.

What is claimed is:

1. A method for measuring the effectiveness of pain management, comprising:
   attaching an activity monitor to a patient, wherein the activity monitor includes at least one sensor;
   collecting sensor data from the sensor;
   filtering the sensor data to obtain filtered sensor data, wherein the filter passes signals associated with defined activities;
   processing the filtered sensor data to obtain measures of the data associated with the defined activities; and
   evaluating the measures to assist in determining the effectiveness of the pain management,
   wherein, following processing the filtered sensor data, the method further includes:
   accumulating the measures into a first data block; and
   tagging the first data block with a stimulation parameter set that is in use when the sensor data was generated to obtain a first tagged data block.

2. The method of claim 1 wherein, following collecting sensor data, the method further includes:
   accumulating the sensor data into a second data block;
   computing gait metrics for stability and smoothness from the data within the second data block;
   determining activity type from the data within the second data block; and
   tagging the gait metrics with the activity type to obtain a second tagged data block.

3. The method of claim 2 further including updating a first stimulation parameter set associated with the pain management whose effectiveness is being measured, wherein updating the first stimulation parameter set comprises:
   processing the first stimulation parameter set, the first tagged data block, and the second tagged data block to provide a second stimulation parameter set;
   comparing the second stimulation parameter set with the first stimulation parameter set to determine if the second stimulation parameter set is more effective than the first stimulation parameter set; and
   if so, replacing the first stimulation parameter set with the second stimulation parameter set.

4. The method of claim 3 further including providing an override option wherein a user may elect to keep the first stimulation parameter set rather than replace it with the second stimulation parameter set.

5. A system for measuring the effectiveness of at least one pain management system, the pain management system having a parameter set associated therewith, the system comprising:
   a sensor that produces sensor data;
   a filter coupled to the sensor that filters the sensor data to produce filtered data, wherein the filter passes signals associated with at least one defined activity;
   a processor coupled to the filter that processes the filtered data to produce measures of the at least one defined activity;
   a first accumulator that accumulates statistics associated with the measures and forms data blocks therefrom; and
   means for tagging the data blocks with the parameter set being used when the sensor data was collected to produce first tagged data blocks.

6. The system of claim 5 further comprising:
   a second accumulator adapted to form second data blocks from the filtered data;
   means for processing the second data blocks to form gait metrics data blocks;
   means for processing the second data blocks to determine an activity type corresponding to the data in the second data blocks; and
   means for tagging the gait metrics data blocks with the activity type corresponding to the data in the second data blocks used to produce second tagged data blocks.

7. The system of claim 6 further including:
   means for processing the parameter set being used, the first tagged data blocks and the second tagged data blocks in order to evaluate the performance of the parameter set being used; and
   means for updating the parameter set being used with an updated parameter set when the performance of the parameter set being used falls below specified criterion.

8. The system of claim 7 wherein the sensor is an accelerometer.

9. The system of claim 8 wherein the means for updating the parameter set includes:
   means for defining an updated parameter set;
   means for applying the updated parameter set to the pain management system;
   means for producing first tagged data blocks and second tagged data blocks using the updated parameter set;
   means for computing a score from the first tagged data blocks and the second tagged data blocks corresponding to the updated parameter set;
   means for comparing the scores computed for the updated parameter set with a corresponding score computer for the parameter set used prior to the updated parameter set; and
   means for selecting the parameter set having the best score as the parameter set to be used by the pain management system.

10. The system of claim 8 wherein the means for updating the parameter set includes:
    means for selecting an initial parameter set;
    means for applying small perturbations to the initial parameter set, wherein the perturbations define candidate stimulation parameter sets which deviate in several different directions away from the parameter set being used;
    means for testing all of the parameter sets and recording scores for each parameter set;
    means for selecting the perturbation associated with the initial parameter set that provided the greatest score as a best perturbation;
    means for computing a new parameter set that steps in the direction defined by the best perturbation;

means for computing the score for the new parameter set;

means for computing another new parameter set moving in the direction of the best perturbation if the score for the new parameter set exceeds previous scores; and means for selecting another initial parameter set and beginning the process described above if the score for the new stimulation parameter set is less than previous scores.

11. An Automatic Stimulation Parameter Adjustment (ASPA) system comprising:

a pain management system that reduces pain in a patient, wherein the pain management system exercises a stimulation parameter set;

a sensor adapted to generate sensor data;

a Sensor Data Acquisition (SDA) system including:
means for filtering the sensor data to generate filtered sensor data associated with selected activities; and
means for computing levels of the selected activities from the filtered sensor data;

an Automated Exertion Monitoring (AEM) system including:
means for accumulating a multiplicity of first data blocks of the levels of the selected activities; and
means for tagging the first data blocks with a tag to form tagged data blocks, wherein the tag provides information regarding the stimulation parameter set in use when the sensor data resulting in the data blocks was acquired;

a Walking Gait Monitoring (WGM) system including:
means for accumulating filtered sensor data into second data blocks;
means for computing gait metrics from the second data blocks;
means for determining activity type from the second data blocks; and
means for tagging the gait metrics with the activity type to form tagged gait metrics;

an update system parameters function, wherein the update system parameters function includes means for updating the stimulation parameters based on the present stimulation parameters, the tagged data blocks, and the tagged gait metrics.

12. The system of claim 11 wherein the pain management comprises a Spinal Cord Stimulation (SCS) system, and wherein the SCS system includes an Implantable Pulse Generator (IPG) connected to an implantable electrode array, and wherein the IPG includes means for providing electrical current to the electrode array.

13. The system of claim 11 wherein the sensor includes an accelerometer.

14. The system of claim 11 wherein the means for filtering comprises a bandpass filter with a pass band between about 0.1 Hz and 5 Hz.

* * * * *